United States Patent [19]

Higuchi

[11] 4,439,196
[45] Mar. 27, 1984

[54] OSMOTIC DRUG DELIVERY SYSTEM

[75] Inventor: Takeru Higuchi, Lawrence, Kans.

[73] Assignee: Merck & Co., Inc., Rahway, N.J.

[21] Appl. No.: 359,447

[22] Filed: Mar. 18, 1982

[51] Int. Cl.³ .............................................. A61K 9/22
[52] U.S. Cl. .................................................. 604/890
[58] Field of Search ............................... 604/890–900; 424/19–25

[56] References Cited

U.S. PATENT DOCUMENTS

| | | |
|---|---|---|
| 3,845,770 | 8/1976 | Theeuwes et al. |
| 3,975,350 | 7/1976 | Hudgin et al. |
| 3,982,536 | 8/1976 | Krogseng et al. |
| 3,993,072 | 12/1976 | Zaffaroni |
| 4,014,334 | 9/1978 | Theeuwes et al. |
| 4,093,708 | 8/1978 | Zaffaroni et al. |
| 4,160,452 | 7/1979 | Theeuwes |
| 4,210,139 | 7/1980 | Higuchi |
| 4,298,003 | 11/1981 | Theeuwes et al. |
| 4,309,996 | 1/1982 | Theeuwes |

Primary Examiner—Benjamin R. Padgett
Assistant Examiner—T. J. Wallen
Attorney, Agent, or Firm—Rudolph J. Anderson; Mario A. Monaco, Jr.; Michael C. Sudol, Jr.

[57] ABSTRACT

An osmotic drug (or other beneficial substance) delivery system comprises a multi-chamber compartment formed by an external shell and one or more chamber-dividing walls each with a small orifice, of a microporous material and overlayers of semipermeable membranes completely covering the outer shell of all but one chamber and substantially covering the outer shell of the remaining chamber. Osmotic agents, adjuvants, enzymes, drugs, pro-drugs, pesticides and the like are incorporated in the chambers covered by the semipermeable membrane, and external fluids that diffuse into those chambers form solutions and by osmotic pressure are forced through the orifice to the drug chamber to form a solution thereof and then through the exposed microporous shell to the exterior of the device at a rate controlled by the permeability of the semipermeable overlay and the osmotic pressure gradient across the shell.

14 Claims, 2 Drawing Figures

OSMOTIC DRUG DELIVERY SYSTEM

BACKGROUND OF THE INVENTION

This invention is concerned with an osmotic drug (or other beneficial substance) delivery system comprising a multi-chamber compartment formed by an external shell and one or more chamber-dividing walls each with a small orifice, of a microporous material and overlayers of semipermeable membranes completely covering the outer shell of all but one chamber and substantially covering the outer shell of the remaining chamber. Osmotic agents, adjuvants, prodrugs, enzymes, drugs, pesticides, and the like are incorporated in the chambers covered by the semipermeable membrane, and external fluids that diffuse into those chambers form solutions and by osmotic pressure are forced through the orifice to the drug chamber to form a solution thereof and then through the exposed microporous shell to the exterior of the device at a rate controlled by the permeability of the semipermeable overlay and the osmotic pressure gradient across the shell.

By this means there is provided a device for the administration or an active agent at a controlled and continuous rate to achieve a predetermined useful effect in animals including humans.

The advantages of controlled, prolonged release of medicinal agents is well known and several devices for that purpose have been described. Many of these have certain disadvantages which are catalogued in U.S. Pat. No. 3,845,770, which itself describes a controlled release drug delivery system.

The delivery system of U.S. Pat. No. 3,845,770 dispenses a solution of the active agent through a minute orifice in the wall of the device. Such a system tends to administer the active agent at relatively high concentration to a relatively small area of body tissue. In addition the orifice through which the active agent is dispensed can be subject to mechanical plugging. On the other hand, the microporous structure through which the active agent is dispensed in the novel device of the present application distributes the drug from a larger surface, hence larger area of tissue, favoring more rapid and ready absorption without local toxic reaction. In addition there is no propensity to plug as with the prior art device.

Accordingly, it is an object of this invention to:

provide a novel dispensing device for the dispensing of a composition of matter to produce a beneficial effect, which device overcomes the aforesaid disadvantages associated with the prior art devices;

provide a novel dispensing device for dispensing a composition of matter at a controlled rate for a prolonged period of time;

provide a novel and useful dispensing device that is simple in construction, designed with a minimum number of parts, easy to use, and in operation exhibits all the practical and useful benefits obtained by the controlled, continuous long-term administration of various compositions of matter, that is, active agents to animals, avians, humans and into other receptive environments;

provide a novel dispensing device that can administer a complete pharmaceutical dosage regimen for a particular time period, the use of which requires intervention only for initiation and termination of the regimen;

provide an improved dispensing device which will permit high concentration of an active agent to be contained therein, and which high concentration will not exhibit the tendency to be leached from the device nor have its potency decreased by chemical breakdowns;

provide a novel product dispensing device that contains a product which can be used as an osmotically effective solute to exhibit an osmotic pressure gradient against an external fluid;

provide a product dispensing device that contains a product in a form suitable for storage thereby giving the device an improved shelf life;

provide a dispensing device for the administration of locally acting or systemically acting drugs to produce a physiologic or pharmacologic effect and which device can release the drug at a rate that does not vary with time;

provide a device containing drugs in various physiochemical forms such as esters, salts and the like that can be heat sterilized by conventional techniques;

provide a device for dispensing an active agent which device can have a variety of release rates ranging from very low to very high by using polymeric wall forming materials in combination with the active agent or a mixture of an active agent and another osmotically effective compound;

provide a novel and useful erodible or biodegradable device that erodes or degrades after the device has released the active agent;

provide a novel dispensing device with the above-described attributes in a variety of shapes and sizes designed for oral ingestion, implantation, or rectal, vaginal, or ocular insertion.

Other objects, features, and advantages of the invention will be apparent to those skilled in the art from the detailed description of this specification, taken in conjunction with the drawings and the accompanying claims.

DESCRIPTION OF THE DRAWINGS

The drawings are examples of the novel delivery sytem of this invention in a shape suitable for a rectal suppository, but it is to be understood that they are exemplary only and that other shapes and sizes for other modes of administration that function in the same manner fall within the purview of this invention.

DETAILED DESCRIPTION OF THE INVENTION

The novel device of this invention is an osmotic delivery system shaped and sized for oral ingestion, implantation, rectal, vaginal or ocular insertion for delivery of a drug or other beneficial substance comprising a compartment consisting of 2 or more chambers in series, the chambers being adapted to house osmotically active agents, adsorption adjuvants, drugs, and pro-drugs, the chambers being formed by an external shell and 1 or more chamber-dividing walls, each chamber-dividing wall having a micro-orifice connecting adjacent chambers, the external shell and chamber-dividing walls being of a rigid microporous material; one or more successive overlayers of a semipermeable membrane, the first overlayer completely covering the external shell of all but one chamber and substantially covering the external shell of the one chamber leaving exposed a microporous drug-emitting surface; and each successive overlayer completely covering all but one more chamber and substantially covering the one more chamber; and optionally including a quick release loading dose of drug external to and covering the microporous drug-emitting surface.

Figure 1:
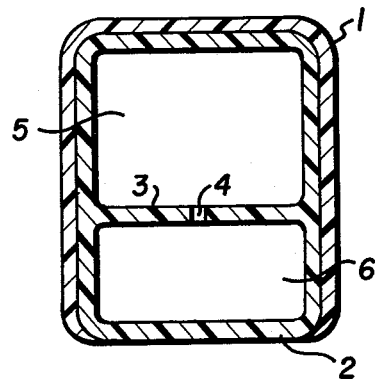
FIG. 1 is a cross-section of a novel device of this invention with two chambers, showing the semi-permeable membrane overlay, 1, the microporous rigid shell, 2, the dividing wall, 3, with the orifice, 4, separating chamber 5 containing osmotic agents, and chamber 6 containing the active agent.

The upper part of the novel device of this invention with 2 chambers consists of a chamber (FIG. 1, 5) containing an osmotically active agent which may or may not be a pharmacologically active agent or pro-drug, especially a relatively soluble pro-drug form of a relatively insoluble drug. The shell of that chamber is designed to be relatively inflexible but semipermeable to water. The semipermeability to water and suitable rigidity can be obtained, for example, by coating a microporous, rigid shell (FIG. 1, 2) of a relatively hard, preferably biodegradable polymer, with an appropriate semipermeable substance (FIG. 1, 1). The pores of the shell of the upper chamber may or may not be filled with the osmotically active agent.

The lower chamber of the novel device (FIG. 1, 6), which can be formed externally from the same microporous substance as in the upper part, but not necessarily is filled with the drug or other beneficial substance to be delivered or an appropriate formulation thereof including, but not necessarily, additional osmotically active agent. The upper and lower chambers are connected and separated by a chamber-dividing wall (FIG. 1, 3) with a small orifice (FIG. 1, 4) opening into the two chambers. The porosity of the shell of the lower chamber is selected so as to maintain a small positive pressure within the chamber with respect to the exterior during use of the device.

In its operation, the device is introduced to the appropriate site such as the rectum, muscle, gastrointestinal tract, vagina, or cul de sac. Because of the substantial area of the semipermeable membrane exposed by the upper part of the device, water is slowly drawn into the upper chamber from the adjacent tissue by osmotic action, at a rate controlled by the water permeability of the semipermeable membrane. The aqueous solution which is produced in the upper chamber at a more or less constant rate by this process flows through the orifice connecting the two chambers and eventually carries with it the drug substance stored in the lower chamber through the microporous shell. The overall rate of delivery is determined by the total osmotic volume flow rate generated across the semipermeable membrane and the amount of the drug substance transported to the surface of the device per unit volume of the osmotically-produced aqueous fluid.

Although in FIG. 1 the orifice connecting the lower and upper chambers is shown to be a simple opening offering no significant resistance to flow, it is possible for the present invention to utilize a controlling valve in its place to create a significant improvement in the use of the invention for special purposes. Thus one of the features of the invention is the possibility of controlling the manner of delivery other than that of constant flow or zero order delivery.

One special embodiment of this capability is to incorporate a valve in place of the orifice which will not allow any significant flow to take place until a certain preselected pressure develops in the upper chamber. At this pressure, the flow will take place until the pressure is substantially relieved. The valve closes at this point and will not open again until the preset pressure is again reached. This intermittent mode of flow will produce pulsed delivery of the drug substance to the surface of the device according to any special requirement. This mode of rectal drug delivery is of special advantage when absorption adjuvants are to be co-administered. Continuous mode of delivery may not present to the absorbing tissue high concentrations simultaneously of both the drug and adjuvant. Pulsed delivery will permit this to take place more effectively. The interval between pulses may be as short as 10 to 20 minutes or as long as several hours.

Another embodiment of the present invention includes a quick-releasing loading dose of the drug substance external to the drug reservoir on the surface of the microporous shell which would eventually serve as the drug-emitting surface. This is a desirable feature since the pumping action will not take place immediately on insertion of the device.

Figure 2:
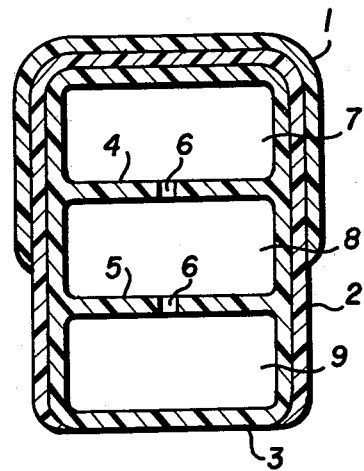
FIG. 2, also is a cross-section of a novel device of this invention with three chambers, showing a relatively resistant semipermeable membrane overlay, 1, a relatively permeable semi-permeable membrane 2, the microporous shell 3, dividing walls, 4 and 5, with orifices, 6, separating chamber 7 containing an absorption adjuvant, chamber 8, containing an osmotic agent, and chamber 9 containing the active agent.

Another embodiment of this invention is that which is specially desirable when adjuvants are to be co-delivered by the device or the active agent is to be delivered slowly by means of dilute solutions. Although the configuration shown in FIG. 1 may often suffice where the adjuvant may be included in the upper chamber and/or the lower chamber, in some instances the design shown in FIG. 2 offers greater flexibility in selection of both the osmotic and adjuvant agents. In this configuration, there are three chambers with the adjuvant being placed in the upper most chamber which has a (FIG. 2, 7) semipermeable external barrier of relatively low permeability. The middle chamber will contain largely appropriate osmotic agent and will present a relatively highly semipermeable (aqueous) barrier surface to the outside. The bottom chamber still serves as the drug reservoir. This design will permit greater flexibility in selecting both the osmotic agent and the adjuvant. The difference in the mode of operation between the designs shown in FIG. 1 and FIG. 2 is apparent in that with the former if a solid adjuvant is present in the upper chamber serving both as a source of the adjuvant and as the osmotic agent, the adjuvant will surface outside the drug reservoir more or less as a saturated solution. In the second configuration, however, the adjuvant can be delivered in a substantially diluted, subsaturation concentration because of the diluting effect produced by influx of water into the second chamber. It is evident that this will permit greater flexibility in use of the invention for various drugs and various adjuvants and will allow closer approach to optimal temporal pattern for a given drug.

In the configuration represented schematically in FIG. 2, pulsed delivery can be effected by placing the valving system between the second and third chamber.

Although there is no limit to the number of chambers that can be incorporated in the novel device of this invention, for various specialized purposes, it is preferred that it have not more than 3 and preferably only 2 chambers.

The substance forming a large part of the outer surface of the novel device of this invention is semipermeable, for example a material that is permeable to an external fluid such as water and the like while essentially impermeable to a selected product or other compounds in the device. This material can be non-erodible or bioerodible after a predetermined period of time and in each instance it is semi-permeable to solvent but not to solute and is suitable for construction of the outer layer of the device. Typical materials for forming the wall include membranes known to the art as osmosis and reverse osmosis membranes such as commercially available unplasticized cellulose acetate, plasticized cellulose acetate, reinforced cellulose acetate, cellulose nitrate with 11 percent nitrogen, cellulose diacetate, cellulose triacetate, agar acetate, amylose triacetate, beta glucan acetate, beta glucan triacetate, cellulose acetate, acetaldehyde dimethyl acetate, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose acetate butyl sulfonate, cellulose acetate proprionate, cellulose acetate p-toluene sulfonate, triacetate or locust gum bean, cellulose acetate with acetylated hydroxyethyl cellulose, hydroxylated ethylene-vinylacetate, cellulose acetate butyrate having a viscosity of from about 10 seconds to about 50 seconds, cellulose acetate butyrate containing about 17 percent of combined butyryl and about 29.5 percent acetyl, permselective, aromatic nitrogen-containing polymeric membranes that exhibit water permeability and essentially no solute passage, osmosis membranes made from polymeric epoxides, osmosis membranes made from copolymers of an alkylene oxide and alkyl glycidyl ether, semi-permeable polyurethanes, semi-permeable polyglycolic or polylactic acid and derivatives thereof, thin film membranes as disclosed by Loeb and Sourirajan in U.S. Pat. No. 3,133,132, the membranes of ionically associated polyelectrolytes, the polymers formed by the coprecipitation of polycation and a polyanion as described in U.S. Pat. Nos. 3,276,586; 3,541,005; 3,541,006; 3,546,142; 3,173,876; derivatives of polystyrene such as poly(-sodium styrenesulfonate) and poly(vinylbenzyltrimethyl-ammonium chloride), and the like. Generally, membranes, having a fluid permeability of 0.01 to 10 cc/cm²/hour or day/or higher at atmosphere pressure against a saturated product solution or saturated solute solution to a changing concentration at the temperature of use while simultaneously possessing a high degree of impermeability to the product or solute are useful and within the spirit of the invention.

The preferred materials are the cellulose acetates, especially cellulose triacetate.

The microporous material from which the rigid shell is composed can be described as having a sponge-like appearance that provides a supporting structure for microscopic-sized interconnected pores or voids. The materials can be isotropic wherein the structure is homogenous throughout a cross-sectional area, or they can be anisotropic wherein the structure is non-homogenous throughout a cross-sectional area. The pores can be continuous pores that have an opening on both faces of microporous material, pores interconnected through tortuous paths of regular and irregular shapes including curved, curved-linear, randomly oriented continuous pores, and other porous paths discernible by microscopic examination. Generally microporous materials are defined by the pore size, the number of pores, the tortuosity of the microporous path and the porosity which relates to the size and the number of pores. The pores size of microporous material is easily ascertained by measuring the observed pore diameter at the surface of the material under the electron microscope. Generally, materials possessing from 5 to 95% pores and having a pore size of from 10 angstroms to about 100 microns can be used for making the device. The pore size and other parameters characterizing the microporous structure also can be obtained from flow measurements as discussed in U.S. Pat. No. 3,977,404.

Microporous materials are commercially available materials and can be made by art known methods. The materials can be made by etched nuclear tracking, by cooling a solution of flowable polymer below the freezing point whereby solvent evaporates from the solution in the form of crystals dispersed in the polymer and then curing the polymer followed by removing the solvent crystals, by cold or hot stretching at low or high temperatures until pores are formed, by leaching from a polymer a soluble component by an appropriate solvent, by ion exchange reaction, and by polyelectrolyte processes. Processes for preparing microporous materials are described in Synthetic Polymer Membranes, by R. E. Kesting, Chapters 4 and 5, 1971, published by McGraw Hill, Inc.; Chemical Reviews, Ultrafiltration. Vol. 18, pages 373 to 455, 1934; Polymer Eng. and Sci., Vol. 11, No. 4, pages 284 to 288, 1971; J. Appl. Poly. Sci., Vol. 15, pages 811 to 829, 1971; and in U.S. Pat. Nos. 3,565,259, 3,615,024; 3,751,536; 3,801,692, 3,852,224; and 3,849,528.

Microporous materials useful for making the devices include microporous polycarbonates comprised of linear polyesters of carbonic acid in which carbonate groups recur in the polymer chain, microporous materials prepared by the phosgenation of a dihydroxyl aromatic such as bisphenol A, poly(vinylchloride), microporous polyamides such as polyhexamethylene adipamide, microporus modacrylic copolymers including those formed of poly(vinylchloride) 60% and acrylonitrite, styrene-acrylic and its copolymers, porous polysulfones characterized by diphenylene sulfone groups in a linear chain thereof, halogenated poly(vinylidene), polychloroethers, acetal polymers, polyesters prepared by esterification of a dicarboxylic acid or anhydride with an alkylene polyol, poly(alkylenesulfides), phenolic polyesters, asymmetric porous polymers, cross-linked olefin polymers, hydrophobic or hydrophilic microporous homopolymers, copolymers or interpolymers having a reduced bulk density, and materials described in U.S. Pat. Nos. 3,595,752; 3,643,178; 3,654,066; 3,709,774; 3,718,532; 3,803,061; 3,852,224; 3,853,601; and 3,852,388, in British Pat. No. 1,126,849, and in Chem. Abst., Vol. 71, 4274f, 22572f, 22573f, 1969.

Additional microporous materials include, polyolefins, poly(urethanes), cross-linked, chain-extended poly(urethanes), microporous poly(urethanes) in U.S. Pat. No. 3,524,753, poly(imides), poly(benzimidazoles), collodion (ceilulose nitrate with 11% nitrogen), regenerated proteins, semi-solid cross-linked poly(vinylpyrrolidone), microporous materials prepared by diffusion of multivalant cations into polyelectrolyte sols as in U.S. Pat. No. 3,565,259, anisotropic permeable microporous materials of ionically associated polyelectrolytes, porous polymers formed by the coprecipitation of a polycation and a polyanion as described in U.S. Pat. Nos. 3,276,589, 3,541,005, 3,541,006, and 3,546,142, derivatives of poly(stryrene) such as poly(sodium styrenesulfonate) and poly(vinyl benzyltrimethylammonium chloride), the microporous materials disclosed in U.S. Pat. No. 3,615,024, and U.S. Pat. Nos. 3,646,178 and 3,852,224. Other microporous materials include those that slowly erode over time, or erode after the device has released the agent; such as, cross-linked gelatin, cross-linked poly(lactide), cross-linked poly(vinyl alcohol) and poly(glycolide).

The preferred microporous materials are fabricated from the cellulosics described earlier, preferably the cellulose triacetate.

Representative of compositions of matter that can be released from the device and can function as a solute are without limitation those compositions soluble in aqueous type fluids such as tear fluid, tissue juices, water; organic solvents and the like. The expression "composition of matter" as used in this disclosure is meant to include the terms product, active agent, beneficial agent and the like, and these terms are deemed as functionally equivalent for the present invention. These compositions are osmotically effective as solutes since they can generate a solvent concentration gradient between the exterior medium and the medium inside the device. These compositions include organic and inorganic compounds such as ephedrine hydrochloride, ephedrine sulfate, hydroxyamphetamine, isoproterenol hydrochloride, carbachol, pilocarpine hydrochloride, pilocarpine nitrate, demecarium bromide, ecothiophate iodide, physostigmine salicylate, timolol maleate, homatropine hydrochloride, homatropine methylbromide, methscopolamine nitrate, alverine citrate, chlorphenoxamine, hydrochloride, calcium pantothenate and the like. Additional compositions that can be administered are those that produce a physiologically or pharmacalogically useful effect at a point in near relation to the delivery device, or compositions that will produce a physiological or pharmacological response at a site remote from the point of release from the device include drugs generically known as, without limitation, hypnotics, sedatives, psychic energizers, tranquilizers, anticonvulsants, muscle relaxants, analgesics, anti-inflammatories, anesthetics, anti-spasmodics, anti-ulcer agents, anti-microbials, hormonal agents, cardiovascular agents, diuretics, neoplastic agents, and the like.

The composition, drug or the like can also be in various forms, such as uncharged molecules, components of molecular complexes, pharmacologically acceptable salts such as hydrochloride, hydrobromide, sulfate, phosphate, nitrate, borate, acetate, maleate, tartrate, salicylate and the like. For acidic drugs, salts of metals, amines, or organic cations, for example quaternary ammonium can be employed. Furthermore, simple derivatives of the drug such as esters, ethers, amides, and the like which have good solubility characteristics are suitable for the purpose of the invention. Also, a product or drug that is water insoluble can be used in a form that is a water soluble derivative thereof to effectively serve as a solute, and on its release from the device is converted by enzymes, hydrolyzed by body pH, or other metabolic processes to the original form or to a biologically active form. Additionally, the drug formulation can have various art known forms such as solution, dispersion, paste, cream, particle, granule, tablet, emulsions, suspensions, powders and the like.

Various osmotically effective solutes including organic and inorganic compounds are advantageously used when it is desired to release a composition, product, drug or the like having limited solubility from the device. The term "limited solubility" as used herein means that the compound has a solubility of less than about 1% by weight in the external fluid, that is, the ratio of the weight of the compound in solution to the weight of the water of that solution is less than 1 percent. The term includes low, slightly and moderate solubility of the composition in the field. The osmotically effective compounds or solutes confined in the device are a substantial motive force of the device and they exhibit an osmotic pressure gradient against an external fluid across the membrane while the membrane is substantially impermeable to the passage of the osmotically effective solute to prevent loss thereof through the membrane. The solutes are conveniently used by dispensing or homogeneously or heterogeneously mixing a solute or a mixture of solutes with the composition, active agent, product or the like either before they are charged into the compartment or by self mixing after charging a solute and composition into the compartment. In operation, these solutes osmotically attract fluid into the device to produce a solution of the solute which is released from the device concomitantly transporting therewith undissolved and dissolved composition, product, drug or the like. Various osmotically effective solutes include compounds such as magnesium sulfate, magnesium chloride, sodium chloride, lithium chloride, potassium sulfate, sodium carbonate, sodium sulfite, lithium sulfate, calcium bicarbonate, sodium sulfate, calcium sulfate, potassium acid phosphate, calcium lactate, magnesium succinate, tartaric acid, soluble carbohydrates such as raffinose, glucose, mixtures thereof and the like. The solid solute, present initially in excess, can be in any suitable physical form such as particles, crystals, pellets, tablets, strips, film, granules and the like.

The preferred osmotic agents are sodium chloride, sodium carbonate, and calcium bicarbonate.

Additionally, the composition and composition solute can be used in a mixed form by mixing the composition or product with a binder. The product in powdered, granular, piece and the like form, is homogeneously or heterogeneously dispersed in the binder which binder is water soluble or water insoluble but will release the product on contact with water. Typical water soluble binders include polyethylene glycol, gelatin, agar, carboxycellulose, ethylmethylcellulose, polyvinyl alcohol, polyvinylpyrrolidone, water soluble starch derivatives and the like. Typical water insoluble binders that can comprise about 1 to 50 percent of the composition include cellulose acetate, polyurethane, epoxides, and other insoluble binders that permit the free movement of water into the pores of the structure to transport the product from the binder.

The amount of composition present in the device, whether soluble, a derivitized soluble form thereof, is generally non-limited and it is an amount larger than or equal to the amount of the composition that is necessary to osmotically operate the device and on its release from the device is effective for bringing about the product's desired effect. Since the invention contemplates a variety of devices of various sizes and shapes, for a variety of uses, there is no critical upper limit on the amount of product incorporated in the device. The lower limit will depend on osmotic activity, the span of the release of the product and the activity of the product. Generally, the device will contain about 0.01 percent to 90 percent or higher of a product or a mixture of product and solute based on the weight of the product or product solute to the volume of the device, and the like. Typically, the device can be of such size and shape to release 0.01 cc to 5 cc or higher of product contained in the fluid per hour, day or longer, such as 1 cc to 10 cc of product solution for 1 to 10 days, and the like.

The micro-orifice in the wall separating the chambers of the novel delivery device of this invention is appromimately of the same size as described in U.S. Pat. No. 3,845,770 and is about $2 \times 10^{-3}$ to about $8 \times 10^{-3}$ cm in length and about $0.3 \times 10^{-3}$ to about $5 \times 10^{-3}$ cm in diameter.

The technology relating to the fabrication of the novel device of this invention is well known in the pharmaceutical art.

What is claimed is:

1. An osmotic delivery system shaped and sized for oral ingestion, implantation, rectal, vaginal or ocular insertion, for delivery of a drug or other beneficial substance comprising a compartment consisting of 2 or more chambers in series, the chambers being adapted to house osmotically active agents, adsorption adjuvants, drugs, and pro-drugs, the chambers being formed by an external shell and 1 or more chamber-dividing walls, each chamber-dividing wall having a micro-orifice connecting adjacent chambers, the external shell and chamber-dividing walls being of a rigid microporous material; one or more succesive overlayers of a semipermeable membrane, the first overlayer completely covering the external shell of all but one chamber and substantially covering the external shell of the one chamber leaving exposed a microporous drug-emitting surface; and each successive overlayer completely covering all but one more chamber and substantially covering the one more chamber; and optionally including a quick release loading dose of drug external to and covering the microporous drug-emitting surface.

2. The osmotic delivery system of claim 1 shaped and sized for oral ingestion, implantation, rectal, vaginal or ocular insertion, for delivery of a drug or other beneficial substance comprising a compartment with 2 or 3 chambers in series, the chambers being adapted to house osmotically active agents, adsorption adjuvants, drugs, and pro-drugs, the chambers being formed by an external shell and 1 or 2 chamber-dividing walls, each chamber-dividing wall having a micro-orifice connecting adjacent chambers, the external shell and chamber-dividing walls being of a rigid microporous material; an overlayer of a semipermeable membrane completely covering the external shell of all but one chamber and substantially covering the external shell of the remaining chamber; and in the embodiment with 3 chambers, an additional overlayer completely covering the external shell and first overlayer of one chamber and substantially covering the external shell and first overlayer of the second chamber; and optionally including a quick release loading dose of drug external to and covering the microporous drug-emitting surface.

3. The osmotic delivery system of claim 1 shaped and sized for oral ingestion, implantation, rectal, vaginal or ocular insertion, for delivery of a drug or other beneficial substance comprising a compartment with 2 chambers formed by an external shell and a chamber-dividing wall, the chamber-dividing wall having a micro-orifice connecting the adjacent chambers, the external shell and chamber-dividing wall being of a rigid microporous material; and an overlayer of a semipermeable membrane completely covering the external shell of one chamber and substantially covering the external shell of the remaining chamber and optionally including a quick release loading dose of drug external to and covering the microporous drug-emitting surface.

4. The delivery system of claim 1 wherein the microporous material of the external shell and the semipermeable membranes of the overlayers are fabricated from a cellulose acetate.

5. The delivery system of claim 2, wherein the microporous material of the external shell and the semipermeable membrane of the overlayer are fabricated from a cellulose acetate.

6. The delivery system of claim 3, wherein the microporous material of the external shell and the semipermeable membrane of the overlayer are fabricated from a cellulose acetate.

7. The delivery system of claim 1, wherein the micro-orifice connecting the chamber with the drug-emitting surface and the adjacent chamber is a pressure actuated controlling valve.

8. The delivery system of claim 2 wherein the micro-orifice connecting the chamber with the drug-emitting surface and the adjacent chamber is a pressure actuated controlling valve.

9. The delivery system of claim 3 wherein the micro-orifice is a pressure actuated controlling valve.

10. The delivery system of claim 4, wherein the micro-orifice connecting the chamber with the drug-emitting surface and the adjacent chamber is a pressure actuated controlling valve.

11. The delivery system of claim 5, wherein the micro-orifice connecting the chamber with the drug-emitting surface and the adjacent chamber is a pressure actuated controlling valve.

12. The delivery system of claim 6, wherein the micro-orifice is a pressure actuated controlling valve.

13. The delivery system of claims 1, 2, 3, 4, 5, 6, 7, 8, 9, 10, 11, or 12 comprising 2 chambers wherein the first chamber is adapted to house an osmotically active agent and the second chamber is adapted to house a drug or other beneficial substance.

14. The delivery system of claims 1, 2, 4, 5, 7, 8, 10, or 11 comprising 3 chambers wherein the first chamber is adapted to house a composition comprising an absorption adjuvant, the middle chamber is adapted to house a composition comprising an osmotically active agent and the third chamber is adapted to house a composition comprising a drug or other beneficial substance.

* * * * *